(12) United States Patent
Curstedt et al.

(10) Patent No.: US 7,511,011 B2
(45) Date of Patent: Mar. 31, 2009

(54) SYNTHETIC LIPID MIXTURES FOR THE PREPARATION OF A RECONSTITUTED SURFACTANT

(75) Inventors: Tore Curstedt, Parma (IT); Jan Johansson, Parma (IT); Bengt Robertson, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 250 days.

(21) Appl. No.: 10/512,869

(22) PCT Filed: May 12, 2003

(86) PCT No.: PCT/EP03/04937

§ 371 (c)(1),
(2), (4) Date: Apr. 19, 2005

(87) PCT Pub. No.: WO03/097695

PCT Pub. Date: Nov. 27, 2003

(65) Prior Publication Data

US 2005/0176625 A1 Aug. 11, 2005

(30) Foreign Application Priority Data

May 17, 2002 (IT) .............................. MI02A1058

(51) Int. Cl.
*A61K 38/16* (2006.01)

(52) U.S. Cl. .............................................. 514/2; 514/7
(58) Field of Classification Search ....................... None
See application file for complete search history.

(56) References Cited

U.S. PATENT DOCUMENTS 5,653,996 A * 8/1997 Hsu ........................... 424/450
7,053,044 B1 * 5/2006 Curstedt et al. ................ 514/2

FOREIGN PATENT DOCUMENTS

| IT | WO 00/47623 | * | 8/2000 |
| WO | 00/47623 | | 8/2000 |
| WO | 01/76619 | | 10/2001 |

* cited by examiner

*Primary Examiner*—Christopher R. Tate
*Assistant Examiner*—Roy Teller
(74) *Attorney, Agent, or Firm*—Oblon, Spivak, McClelland, Maier & Neustadt, P.C.

(57) ABSTRACT

The invention relates to reconstituted surfactants consisting of artificial phospholipids and peptides able to lower the air-liquid surface tension, more particularly to reconstituted surfactants, comprising special phospholipid mixtures and artificial peptides which are analogues of the natural surfactant SP-C protein for the treatment of respiratory distress syndrome (RDS) and other diseases relates to pulmonary surfactant dysfunctions.

12 Claims, No Drawings

SYNTHETIC LIPID MIXTURES FOR THE PREPARATION OF A RECONSTITUTED SURFACTANT

CROSS REFERENCES TO RELATED APPLICATIONS

This application is a national stage application of International Patent Application No. PCT/EP03/04937, filed on May 12, 2003, and claims priority to Italian Patent Application No. MI02A001058, filed on May 17, 2002, both of which are incorporated herein by reference in their entireties.

The present invention relates to reconstituted surfactants consisting of phospholipids and artificial peptides able to lower surface tension at the air-liquid interface. In particular, the invention relates to reconstituted surfactants comprising particular phospholipid mixtures and artificial peptide analogues of the natural surfactant SP-C protein for the treatment of respiratory distress syndrome (RDS) and other diseases related to pulmonary surfactant dysfunctions.

BACKGROUND OF THE INVENTION

Pulmonary surfactant lowers the surface tension arising at the air-liquid interface of the internal alveolar wall, thus preventing the lungs from collapsing at the end of expiration. Surfactant deficiency is a dysfunction which commonly affects preterm infants and causes RDS, a disease which can be effectively treated with natural surfactants extracted from animal lungs. The main constituents of these surfactant preparations are phospholipids, such as 1,2-dipalmitoyl-sn-glycero-3-phosphocholine commonly known as di-palmitoyl-phosphatidyl-choline (DPPC), phosphatidylglycerol (PG) and surfactant hydrophobic proteins B and C (SP-B and SP-C). The hydrophilic surfactant proteins SP-A and SP-D, which are C-type ($Ca^{2+}$-dependent) collagenous lectins and thought to act primarily in the host-defence system, are normally not included in the surfactant preparations due to the organic solvent extraction procedures employed. Modified natural surfactant preparations obtained from animal tissues are used in current therapeutical practice. These preparations usually consist of the aforementioned components with the exception of hydrophilic proteins, which are removed upon extraction with organic solvents.

Owing to the drawbacks of the surfactant preparations from animal tissues, such as the complexity of the manufacturing and sterilization processes and possible induction of immune reactions, attempts to prepare artificial surfactants have been made.

In the strict sense of the word, artificial surfactants are mixtures of phospholipids only or mixtures of phospholipids and other synthetic lipids. Reconstituted surfactants are artificial surfactants added with hydrophobic proteins—either isolated from animal tissues or obtained through recombinant techniques—or synthetic peptidic derivatives of such proteins.

The properties and the activity of reconstituted surfactants greatly depend not only on the protein/peptide components, but also on the composition of the phospholipid mixture.

DESCRIPTION OF THE INVENTION

It has now been found that dipalmitoyl phosphatidylcholine (DPPC) in admixture with specific palmitoyl oleyl phospholipids is an ideal vehicle for the artificial peptides commonly used in reconstituted surfactants as analogues of natural surfactant proteins SP-C and/or SP-B. In particular, reconstituted surfactants comprising the SP-C analogues disclosed in WO 00/47623 in combination with DPPC and a palmitoyl oleyl phospholipid—preferably selected from palmitoyl oleyl phosphatidylglycerol (POPG) or a mixture of POPG with palmitoyl oleyl phosphatidylcholine (POPC)—in weight ratios ranging from 80:20 to 60:40 have been found to lower the surface tension and the viscosity of the preparations obtained therefrom. Contrary to what is reported in the literature, it has also surprisingly been found that the addition of palmitic acid (PA) is useless and, what's more, in some cases can lower the in vivo surfactant's activity.

Accordingly, the present invention relates to reconstituted surfactants comprising mixtures essentially consisting of dipalmitoyl phosphatidylcholine (DPPC) and palmitoyl oleyl phosphatidylglycerol (POPG) or a mixture thereof with palmitoyl oleyl phosphatidylcholine (POPC) in weight ratios ranging from 80:20 to 60:40 and artificial peptide analogues of natural surfactant proteins SP-C and/or SP-B. The surfactant of the invention is devoid of palmitic acid.

The weight ratio between DPPC and POPG ranges preferably from 75:25 to 65:35, and is more preferably 68:31. In the case of DPPC:POPG:POPC mixtures, the phospholipids are preferably used in weight ratios of 60:20:20 or 68:15:16.

Any artificial peptide analogue of natural surfactant proteins SP-C and/or SP-B can be advantageously used, such as those disclosed in WO 89/06657, WO 92/22315 and WO 95/32992. Preferred is the use of SP-C analogues having the following general formula (I), the amino acids being represented with the one-letter code,

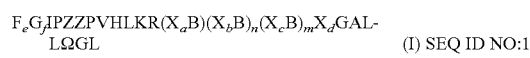
(I) SEQ ID NO:1 wherein:

X is an amino acid selected from the group consisting of I, L, nL (norleucine);

B is an amino acid selected from the group consisting of K, W, F, Y, ornithine;

Z is S optionally substituted with acyl groups containing 12-22 carbon atoms linked to the side chain via an ester or thio-ester bond, respectively;

Ω is an amino acid selected from the group consisting of M, I, L, nL;

a is an integer from 1 to 19;

b is an integer from 1 to 19;

c is an integer from 1 to 21;

d is an integer from 0 to 20;

e is 0 or 1;

f is 0 or 1;

n is 0 or 1;

m is 0 or 1;

with the following provisos:

n+m>0;

f≧e, $(X_aB)_n(X_bB)_n(X_cB)X_d$ is a sequence having a maximum of 22 amino acids, preferably from 10 to 22.

Even more preferred is the use of peptides of formula (II)

(II) SEQ ID NO:2 wherein:

Ω is an amino acid selected from the group consisting of M, I, L, nL and wherein serine can optionally be acylated, for example with palmitoyl.

The hereinafter reported peptide (SP-C33), in the non-acylated form, is the most preferred of the invention,

IPSSPVHLKRLKLLLLLLLLILLLILGALLMGL
(SP-C33) SEQ ID NO:3

Peptides of formula (I) may be prepared by means of conventional peptide synthesis or recombinant techniques as disclosed in WO 00/47623.

Acylated peptides are preferably synthesized by reacting the peptides with an acyl chloride in pure trifluoroacetic acid for 10 hours at room temperature, followed by quenching with 80% aqueous ethanol.

The activity of the reconstituted surfactants of the invention in reducing surface tension has been evaluated both in vitro and in vivo. In particular, the in vivo results clearly show that the reconstituted surfactants of the present invention are able to increase tidal volume—which is in turn an index of the pulmonary expansion capacity—in a significantly higher extent than the surfactants obtained with the mixtures of DPPC, PG and PA commonly used in the prior art.

The reconstituted surfactants of the invention may comprise SP-B or polymixins, in particular polimixin B, as SP-B analogues.

The surfactant can be prepared by mixing solutions or suspensions of peptides and phospholipids and by subsequently drying the mixture. If necessary, the dried mixture can be re-suspended, dispersed or administrated as such to subjects which require a treatment for surfactant deficiency.

In the case of aerosol administration, it will be necessary to combine small surfactant particles with a suitable inert propellant. Other administration forms, such as vapourisation or nebulization of stable surfactant solutions/suspensions, are also within the scope of the present invention.

The following examples illustrate the invention in greater detail.

EXAMPLES

Experimental Section
Materials
1,2-Dipalmitoyl-sn-glycero-3-phosphocholine (DPPC), 1-palmitoyl-2-oleoyl-sn-glycero-3-phosphocholine (POPC), 1-palmitoyl-2-oleoyl-sn-glycero-3-phosphoglycerol (POPG), egg phosphatidylglycerol (PG), palmitic acid (PA), and polymyxin B (PxB) sulfate were utilized to prepare the following lipid mixtures and weight ratios: DPPC/PG/PA, 68:22:9; DPPC/POPG/PA, 68:22:9; DPPC/POPC/POPG, 60:20:20; DPPC/POPG/POPC/PA, 57:19:19:5; DPPC/POPC/POPG, 68:16:15 and DPPC/POPG, 68:31.

SP-C33 was synthesized and purified as described in WO 00/47623.

Preparation of Synthetic Surfactants
SP-C33 and lipids in peptide/lipid weight ratios of 0.02:1 were mixed in chloroform/methanol 98:2 (v/v), the solvents were evaporated and the resulting peptide/lipid films were subsequently hydrated in 150 mM NaCl by repeated sonication, at a lipid concentration of 80 or 35 mg/ml. The surfactant samples used for analyses in the pulsating bubble surfactometer were diluted in saline to working concentrations (10 mg/ml surfactant). In some experiments PxB was added up to a final concentration of 2% (w/w) of the lipid concentration. The surfactant which contained SP-C33 in DPPC/PG/PA (68:22:9) provided very viscous suspensions at 80 mg/ml and was difficult to administer to the experimental animals.

Two well known modified natural surfactants, Curosurf (Chiesi Farmaceutici) and Survanta (Abbott) were administered according to the manufacturer's instructions. Curosurf was suspended at 80 mg/ml and 2.5 ml/kg body weight was administered; Survanta was suspended at 25 mg/ml and 4 ml/kg body weight was administered.

Pulsating Bubble Experiments
The dynamic surface properties of SP-C33 surfactants with and without 2% (w/w) PxB were evaluated by a pulsating bubble surfactometer. For these experiments, the surfactant was suspended in saline at a concentration of 10 mg/ml and analysed at 37° C. The sensitivity towards inhibition was tested by adding 40 mg/ml albumin to the surfactant suspension. A bubble communicating with ambient-air was created in a plastic test chamber containing approximately 20 μl of the sample fluid. The bubble radius was oscillated at a rate of 40 cycles/min. from a maximum of 0.55 to a minimum of 0.40 mm, corresponding to a 50% cyclic surface compression. Surface tension values at minimum and maximum bubble size ($\gamma_{min}$, $\gamma_{max}$) were recorded over 5 min. pulsations.

In Vivo Experiments
The surfactant mixtures were assayed in premature newborn rabbits, obtained by hysterectomy at the gestational age of 27 days (term: 31 days). The animals were tracheotomized at birth, kept in plethysmography boxes at 37° C. and ventilated in parallel with 100% oxygen at a frequency of 40 breaths/min. and a 50% inspiration time. Treated animals received 2.5 ml/kg or 4 ml/kg of the above surfactant preparation through a tracheal cannula. Littermates which did not receive any surfactant preparation were used as controls. After instilling the surfactant, peak pressure was first raised to 35 cmH$_2$O per 1 min., to facilitate the distribution of the surfactant in the lungs, then lowered to 25 cmH$_2$O. The animals were then ventilated with a peak pressure of 25 cmH$_2$O for 15 min., thereafter the pressure was lowered first to 20 cmH$_2$O for 5 min., then to 15 cmH$_2$O for 5 min. and raised again to 25 cmH$_2$O for 5 min. Tidal volumes were measured at 5 min. intervals with a pneumotachograph connected to each plethysmograph box.

At the end of the established ventilation period, the animals were sacrificed by intracerebral lidocain injection. Their abdomen was opened and the diaphragm position was inspected for pneumotorax evidences.

Example 1

SP-C33 In Vitro Superficial Activity in Different Lipid Mixtures

The dynamic surface properties of 2% (w/w) SP-C33 in DPPC/PG/PA (68:22:9), DPPC/POPC/POPG (60:20:20), DPPC/POPC/POPG (68:16:15) and DPPC/POPG (68:31) were evaluated with a pulsating bubble surfactometer, which showed $\gamma_{min}$<2 mN/m after 5 min. pulsation for all the mixtures and $\gamma_{max}$<40 mN/m for all the mixtures except for SP-C33 in DPPC/PG/PA (68:22:9), whose $\gamma_{max}$ was 48 mN/m.

Example 2

In Vivo Optimal Effect Without PA

To evaluate the relevance of the lipid composition, we compared the in vivo effects of SP-C33 in the mixtures DPPC/PG/PA (68:22:9), DPPC/POPG/PA (68:22:9) and DPPC/POPG (68:31). SP-C33 in DPPC/POPG (68:31) showed a higher effect than the other two mixtures. The data showed a marked increase in tidal volumes after treatment with SP-C33 in DPPC/POPG (68:31). They also showed that, if the DPPC and acid lipid content is constant, the presence of PA reduces the effect of the treatment. A negative effect of PA on the in vivo activity of the SP-C33-based surfactant is further confirmed by the effect ($V_T$=12 a 15 min. e $V_T$=14 a 25 min.) of SP-C33 in DPPC/POPC/POPG/PA (57:19:19:5) which is slightly lower than that of SP-C33 in DPPC/POPC/POPG (60:20:20).

The invention claimed is:

1. A reconstituted surfactant consisting of an artificial peptide and a phospholipids mixture wherein the artificial peptide is a SP-C analogue of formula (II)

IPSSPVHLKRLKLLLLLLLLILLLILGALLΩGL
(II) (SEQ ID NO:2)

wherein Ω is a residue selected from the group consisting of M, I, L and nL; and wherein the phospholipid mixture consists of dipalmitoyl phophatidylcholine (DPPC) and a palmitoyl oleyl phospholipids selected from palmitoyl oleyl phosphatidylcholine (POPC) or a mixture thereof with palmitoyl oleyl phosphatidylchline (POPC) in a weight ratio ranging from 80:20 to 60:40.

2. The reconstituted surfactant according to claim 1 wherein the artificial peptide is in combination with DPPC and POPG in weight ratios ranging from 75:25 to 65:35.

3. The reconstituted surfactant according to claim 2 wherein the artificial peptide is in combination with DPPC and POPG in a weight ratio of 68:31.

4. The reconstituted surfactant according to claim 1 wherein the artificial peptide is in combination with DPPC, POPG and POPC in a weight ratio of 60:20:20 to 68:15:16.

5. A process for preparing said reconstituted surfactant of claim 1 comprising:
   i) mixing a solution or a suspension of the peptide and the phospholipids; and
   ii) drying the mixture.

6. A dispersion, a suspension or a dry powder comprising the reconstituted surfactant according to claim 1.

7. A method for the treatment of one or more diseases related to a pulmonary surfactant dysfunction, said method comprising administering said reconstituted surfactant according to claim 1 to a patient in need thereof.

8. The method according to claim 7 wherein the disease is respiratory distress syndrome (RDS).

9. A reconstituted surfactant consisting of an artificial peptide of formula

IPSSPVHLKRLKLLLLLLLLILLLILGALLMGL
(SP-C33) (SEQ ID NO:3)

and a phospholipid mixture consisting of dipalmitoyl phosphatidylcholine (DPPC) and a palmitoyl oleoyl phospholidpid selected from palmitoyl oleoyl phosphatidylglycerol (POPG) or a mixture thereof with palmitoyl oleoyl phosphatidylcholine (POPC) in a weight ratio ranging from 80:20 to 60:40.

10. The reconstituted surfactant according to claim 1, wherein the artificial peptide is IPSSPVHLKRLKLLLLLL LLILLLILGALLIGL (SEQ ID NO:4).

11. The reconstituted surfactant according to claim 1, wherein the artificial peptide is IPSSPVHLKRLKLLLLLL LLILLLILGALLLGL (SEQ ID NO:5).

12. The reconstituted surfactant according to claim 1, wherein the artificial peptide is IPSSPVHLKRLKLLLLLLL LILLLILGALLnLGL (SEQ ID NO:6).

* * * * *

SEQUENCE LISTING

<160> NUMBER OF SEQ ID NOS: 6

<210> SEQ ID NO 1
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: May or may not be present
<220> FEATURE:
<221> NAME/KEY: MOD_RES
<222> LOCATION: (13)..(31)
<223> OTHER INFORMATION: Ile, Leu or norleucinecine; Region may
      encompass 1-19 residues
<220> FEATURE:
<221> NAME/KEY: MOD_RES
<222> LOCATION: (32)..(32)
<223> OTHER INFORMATION: Lys, Trp, Phe, Tyr or ornithine
<220> FEATURE:
<221> NAME/KEY: MOD_RES
<222> LOCATION: (33)..(51)
<223> OTHER INFORMATION: Ile, Leu or norleucinecine; Region may
      encompass 1-19 residues
<220> FEATURE:
<221> NAME/KEY: MOD_RES
<222> LOCATION: (52)..(52)
<223> OTHER INFORMATION: Lys, Trp, Phe, Tyr or ornithine
<220> FEATURE:
<221> NAME/KEY: MOD_RES
<222> LOCATION: (33)..(52)
<223> OTHER INFORMATION: Region may or may not be present
<220> FEATURE:
<221> NAME/KEY: MOD_RES
<222> LOCATION: (53)..(73)
<223> OTHER INFORMATION: Ile, Leu or norleucinecine; Region may
      encompass 1-21 residues
<220> FEATURE:
<221> NAME/KEY: MOD_RES
<222> LOCATION: (74)..(74)
<223> OTHER INFORMATION: Lys, Trp, Phe, Tyr or ornithine
<220> FEATURE:
<221> NAME/KEY: MOD_RES
<222> LOCATION: (53)..(74)
<223> OTHER INFORMATION: Region may or may not be present
<220> FEATURE:
<221> NAME/KEY: MOD_RES
<222> LOCATION: (75)..(94)
<223> OTHER INFORMATION: Ile, Leu or norleucinecine; Region may
      encompass 0-20 residues
<220> FEATURE:
<221> NAME/KEY: MOD_RES
<222> LOCATION: (99)..(99)
<223> OTHER INFORMATION: Met, Ile, Leu or norleucine

<400> SEQUENCE: 1

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Gly Ala
                85                  90                  95

Leu Leu Xaa Gly Leu
            100
```

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Met, Ile, Leu or norleucine

<400> SEQUENCE: 2

```
Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Xaa Gly
            20                  25                  30

Leu
```

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Met Gly
            20                  25                  30

Leu
```

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Ile Gly
            20                  25                  30

Leu
```

<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 5

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Leu Gly
            20                  25                  30

Leu

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: norleucine

<400> SEQUENCE: 6

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Leu Gly
            20                  25                  30

Leu
```